United States Patent [19]
Tollini

[11] Patent Number: 5,244,523
[45] Date of Patent: Sep. 14, 1993

[54] BANDAGE FOR REPLACEABLE DRESSING AND METHOD OF FABRICATION THEREOF

[76] Inventor: Dennis R. Tollini, 12 Palmdale Dr., Williamsville, N.Y. 14221

[21] Appl. No.: 834,583

[22] Filed: Feb. 12, 1992

Related U.S. Application Data

[63] Continuation-in-part of Ser. No. 591,546, Oct. 1, 1990, Pat. No. 5,098,399, which is a continuation-in-part of Ser. No. 476,357, Feb. 7, 1990, Pat. No. 4,976,700.

[51] Int. Cl.$^5$ .................... A61F 13/02; B32B 31/18
[52] U.S. Cl. .................. 156/227; 156/252; 156/253; 156/256; 602/900
[58] Field of Search ........... 156/227, 66, 256, 298, 156/299, 252–253; 602/57, 900; 604/179, 180

[56] References Cited

U.S. PATENT DOCUMENTS

| | | | |
|---|---|---|---|
| 3,288,136 | 11/1966 | Lund | 128/133 |
| 3,430,300 | 3/1969 | Doan | 604/180 X |
| 3,556,096 | 1/1971 | Fuller et al. | 128/171 |
| 3,823,713 | 7/1974 | Shah | 128/157 |
| 3,826,254 | 7/1974 | Mellor | 128/133 |
| 3,834,380 | 9/1974 | Boyd | 128/133 |
| 4,165,748 | 8/1979 | Johnson | 128/343 |
| 4,263,906 | 4/1981 | Finley | 128/157 |
| 4,324,237 | 4/1982 | Buttaravoli | 604/180 |
| 4,457,754 | 7/1984 | Buttaravoli | 128/DIG. 26 |
| 4,569,348 | 2/1986 | Hasslinger | 604/179 |
| 4,662,366 | 5/1987 | Tari | 128/877 |
| 4,671,787 | 6/1987 | Widman | 128/DIG. 26 |
| 4,702,736 | 10/1987 | Kalt et al. | 604/180 |
| 4,732,146 | 3/1988 | Fasline et al. | 128/155 |
| 4,737,143 | 4/1988 | Russell | 128/DIG. 26 |
| 4,738,662 | 4/1988 | Kalt et al. | 604/180 |
| 4,822,342 | 4/1989 | Brawner | 604/180 |
| 4,838,878 | 6/1989 | Kalt et al. | 604/180 |
| 4,909,243 | 3/1990 | Frank et al. | 128/156 |
| 4,928,712 | 5/1990 | Mele | 128/877 |

*Primary Examiner*—Caleb Weston
*Assistant Examiner*—R. Crispino
*Attorney, Agent, or Firm*—Joseph P. Gastel

[57] ABSTRACT

A bandage for removably retaining a replaceable dressing against a patient's skin including a tape having an adhesive inner surface with pressure-sensitive adhesive thereon and a nonadhesive outer surface, a base portion on the tape for adhesive securement to a patient's skin, a tab formed integrally with the base portion by a folded-over portion of the tape, a first opening in the base portion for placement over a wound on the patient's skin for receiving the dressing, a second opening in the tab exposing an adhesive portion of the inner surface of the tape for receiving and adhesively holding a pad which overlies the first opening when the tab is in a closed position, and cooperating hook and pile fabric on the tab and the base portion containing the first opening for selectively securing the tab to the base portion. A method of fabricating the above described bandage including the steps of cutting the first and second openings in the tape prior to folding over the central portion, attaching the pad to the exposed adhesive in the second opening of the tab, and attaching the cooperating hook and pile fabric to the tab and base.

17 Claims, 8 Drawing Sheets

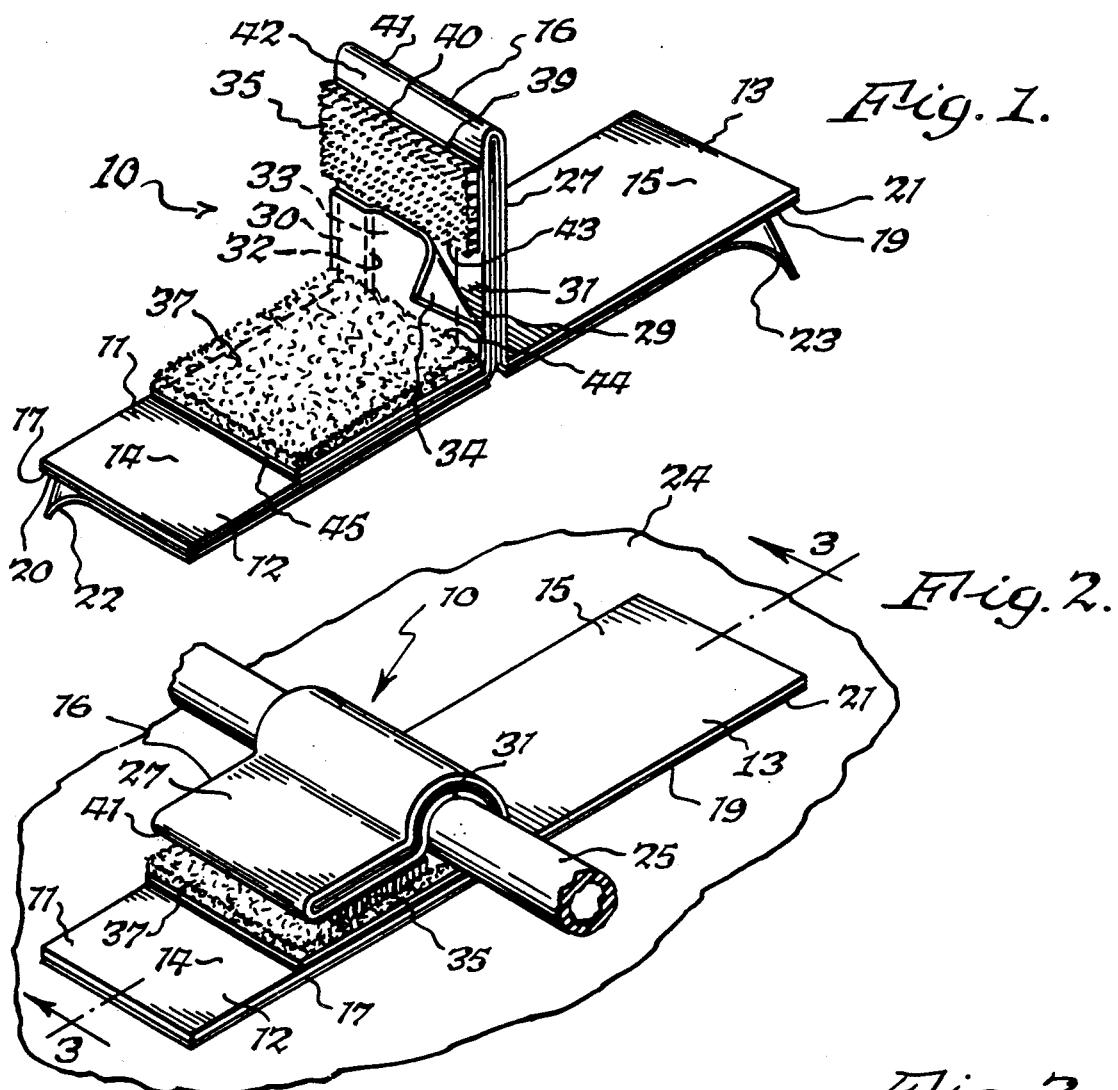
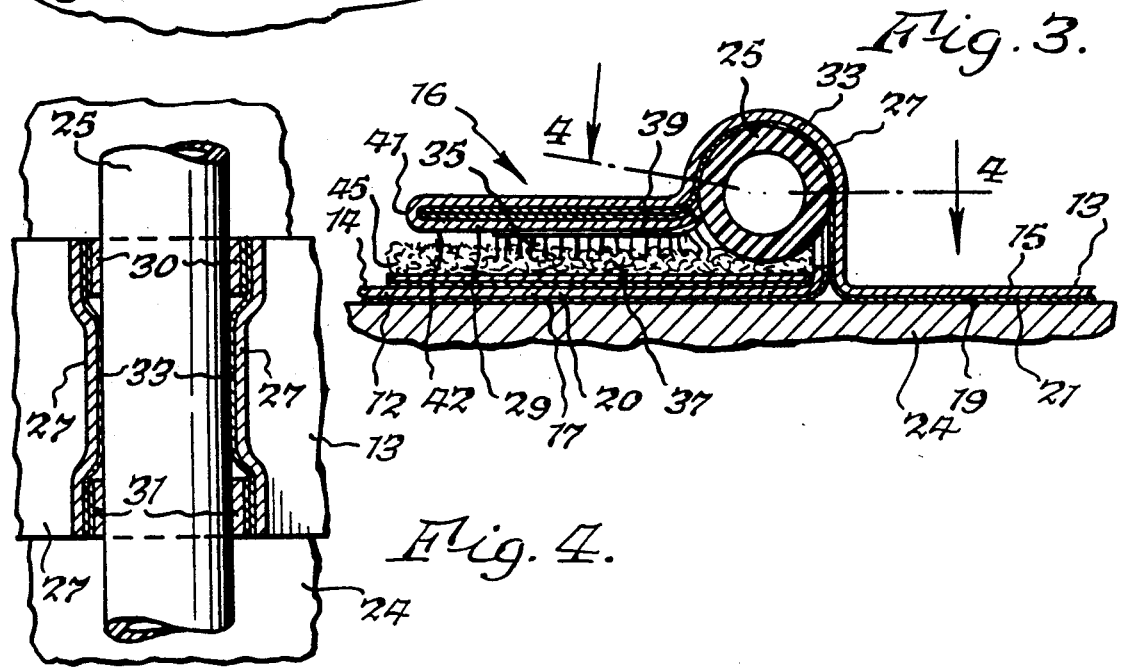

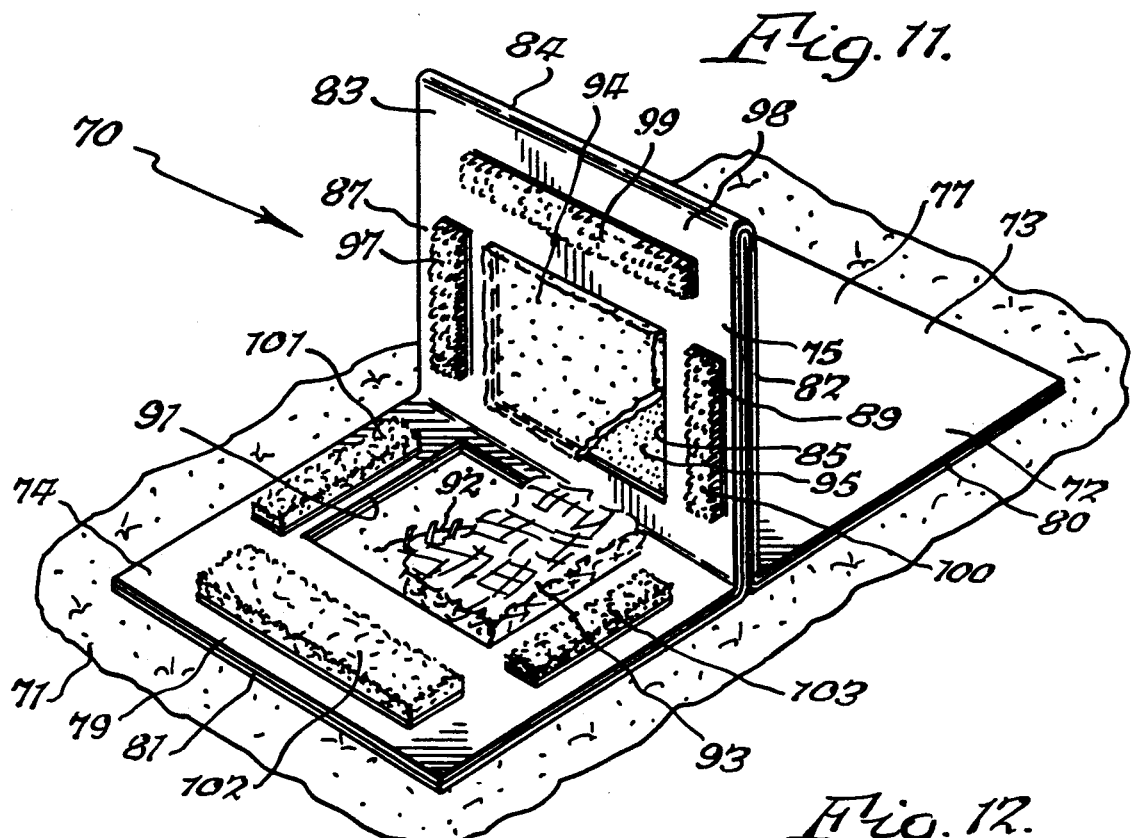
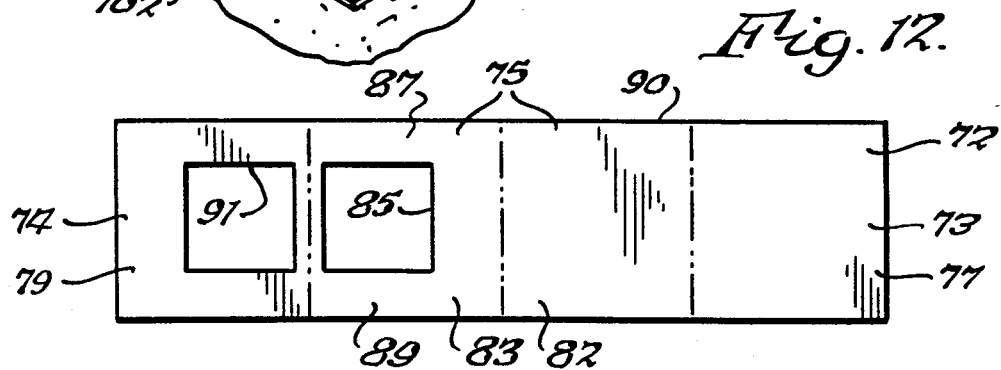
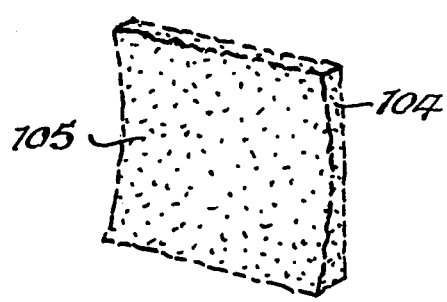
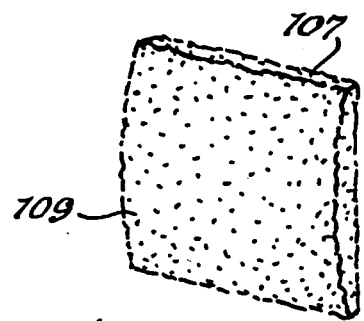

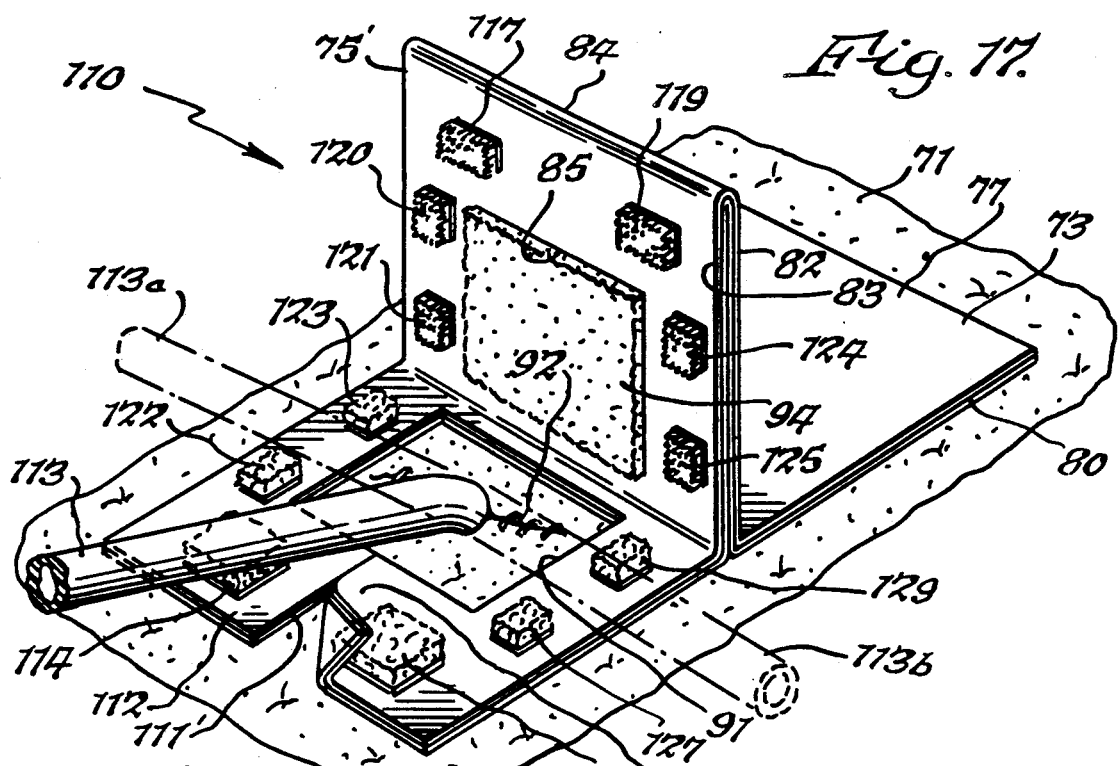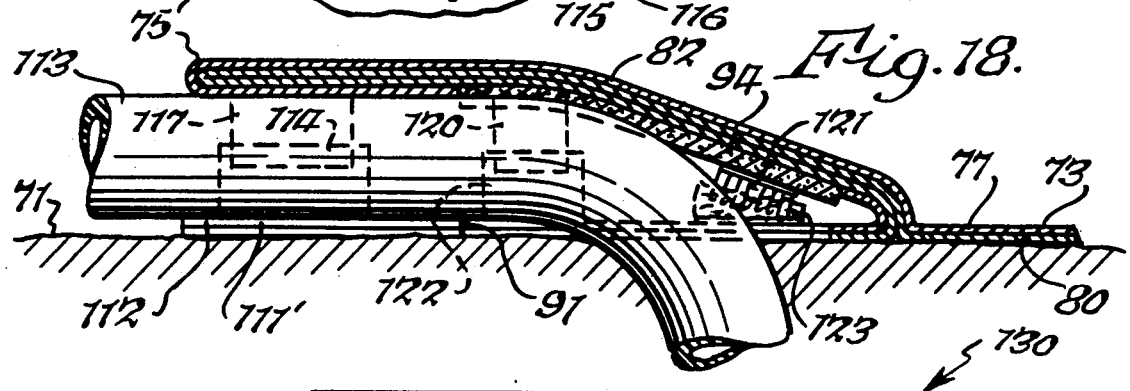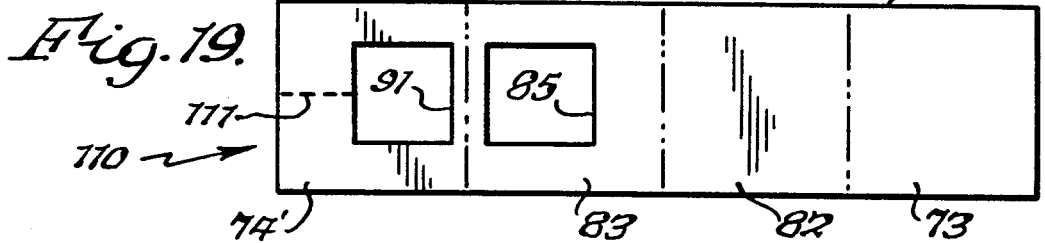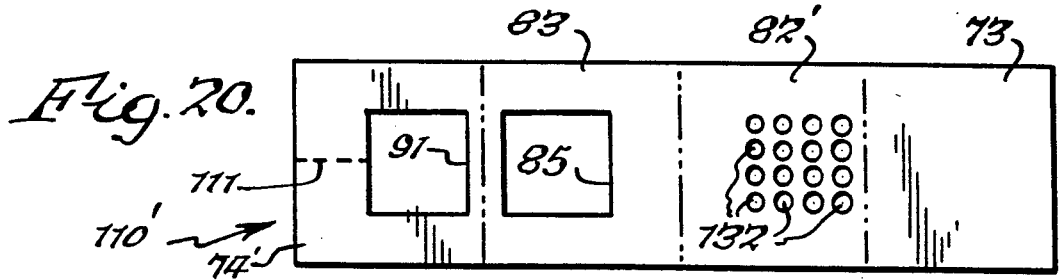

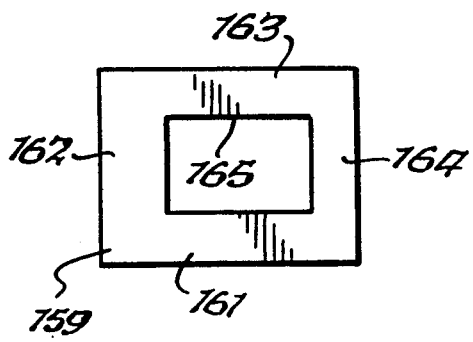
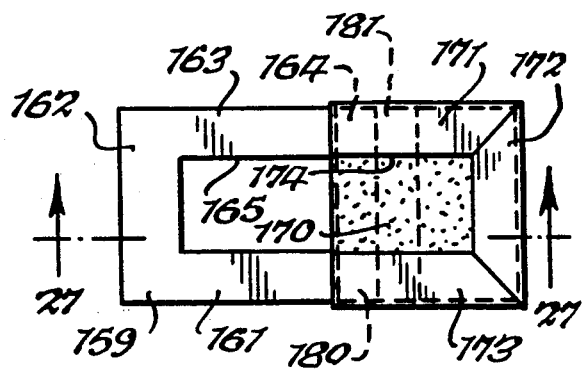
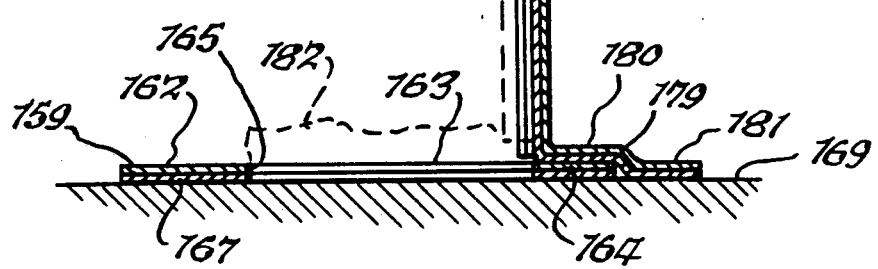
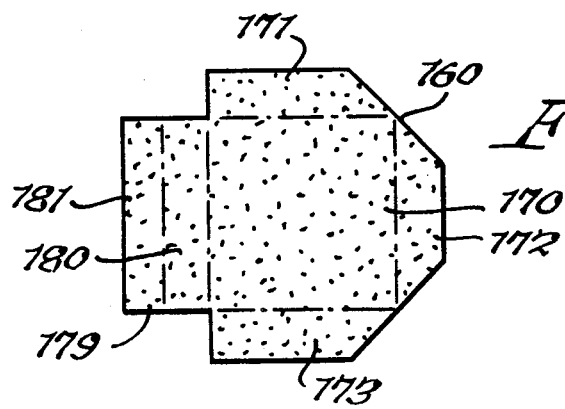

BANDAGE FOR REPLACEABLE DRESSING AND METHOD OF FABRICATION THEREOF

CROSS REFERENCE TO RELATED APPLICATIONS

The present application is a continuation-in-part of application Ser. No. 591,546, filed Oct. 1, 1990, now U.S. Pat. No. 5,098,399, issued Mar. 24, 1992, which is a continuation-in-part of patent application Ser. No. 476,357, filed Feb. 7, 1990, now U.S. Pat. No. 4,976,700, issued Dec. 11, 1990.

BACKGROUND OF THE INVENTION

The present invention relates to an improved medical securing tape in the nature of a bandage for securing replaceable surgical or medical dressings, as well as for securing tubes or catheters, and to a method of fabrication thereof.

By way of background, bandages for securing replaceable dressings are known. However, previous dressings were not basically fabricated out of adhesive tape having an adhesive coating on one side thereof. Furthermore, insofar as known, prior tapes could not conveniently be used with both a replaceable dressing and a tube inserted into a wound while permitting the bandage to be removed without removing the tube.

SUMMARY OF THE INVENTION

It is accordingly one object of the present invention to provide an improved bandage for receiving replaceable dressings which can be fabricated out of tape having an adhesive coating on one side thereof.

Another object of the present invention is to provide an improved bandage such as described in the immediately preceding paragraph which can be used simultaneously with both a replaceable dressing and a tube inserted into a wound and which can be removed from a patient without removing the tube from the wound.

A further object of the present invention is to provide an improved bandage which, when used with a tube, as described in the immediately two preceding paragraphs, will also have a low profile and which will hold the tube against excessive lateral movement.

Yet another object of the present invention is to provide an improved bandage as described in the immediately three preceding paragraphs which also permits a tube associated therewith to be placed in a plurality of different orientations, as desired, relative to a bandage which is previously mounted on a patient's skin.

Still another object of the present invention is to provide an improved method of fabricating a bandage which can be used with replaceable dressings and also simultaneously with a tube inserted into a wound. Other objects and attendant advantages of the present invention will readily be perceived hereafter.

The present invention relates to a bandage for retaining a dressing against a patient's skin comprising a tape having an adhesive inner surface with pressure sensitive adhesive thereon and a nonadhesive outer surface, a base portion on said tape including said adhesive surface for adhesive securement to said patient's skin, opening means in said base portion for placement over a wound on said patient's skin for receiving a dressing when said base portion is secured to said patient's skin, tab means for overlying said opening means, said tab means comprising facing portions of said inner surface adhered to each other, and securing means for securing facing portions of said tab means and said outer surface of said base portion containing said opening means to said base portion with said dressing located in said opening. In its more specific form the tab means comprises an integral extension of the base portion with an exposed adhesive surface for receiving and holding the pad which overlies the dressing.

The present invention also relates to a method of fabricating a bandage for securing to a patient's skin comprising the steps of providing a strip of pressure-sensitive tape having a pressure-sensitive adhesive surface and a nonadhesive surface with release paper overlying the pressure-sensitive adhesive surface, cutting an opening in an end portion of said pressure-sensitive tape, removing the release paper from a central portion of said pressure-sensitive tape adjacent to said end portion, folding the central portion of said pressure-sensitive tape from which said release paper was removed back on itself to provide a tab, the remainder of said pressure-sensitive tape other than said tab but including said end portion providing a base with said opening in said end portion for surrounding a wound and for receiving a dressing, and applying securing means to said pressure-sensitive tape for securing said tab to said nonadhesive surface of said base.

The various aspects of the present invention will be more fully understood when the following portions of the specification are read in conjunction with the accompanying drawings wherein:

BRIEF DESCRIPTION OF THE DRAWINGS

FIG. 1 is a perspective view of the improved securing tape as it is ready for use;

FIG. 2 is a fragmentary perspective view of the securing tape in position on a patient's skin or support and holding a medical device such as a tube;

FIG. 3 is a fragmentary enlarged cross sectional view taken substantially along line 3—3 of FIG. 2;

FIG. 4 is a fragmentary cross sectional view taken substantially along line 4—4 of FIG. 3;

FIG. 11 is a fragmentary perspective view of an embodiment wherein the securing tape functions as a bandage for retaining replaceable dressings against a wound;

FIG. 12 is a plan view of a piece of tape which is used to form the bandage of FIG. 11;

FIG. 13 is a perspective view of a concave pad which may be used in the bandage of FIG. 11;

FIG. 14 is a perspective view of a convex pad which may be used in the bandage of FIG. 11;

FIG. 17 is a fragmentary perspective view showing how the bandage of FIG. 16 may be removed from the patient without removing the tube;

FIG. 18 is a fragmentary cross sectional view taken substantially along line 18—18 of FIG. 16 with the tab in a closed position but with the base severed along the perforations thereon;

FIG. 19 is a plan view of the blank tape which is utilized for the embodiment of FIGS. 16-18;

FIG. 20 is a plan view of the blank tape which is utilized for the embodiment of FIG. 21 for the purpose of permitting the dressing to be ventilated when the tab of the bandage is in a closed position;

FIG. 24 is a plan view of a base for another embodiment of a two-piece bandage;

FIG. 25 is a plan view of a blank for a combined tab and base which is to be used with the base of FIG. 24;

FIG. 26 is a plan view of a tab and base which have been formed from the blank of FIG. 25 with the base in its operative position relative to the base of FIG. 24;

FIG. 27 is a cross sectional view taken substantially along line 27—27 of FIG. 26 and showing the assembled two-piece bandage with the tab in an elevated position;

DESCRIPTION OF THE PREFERRED EMBODIMENTS

Figure 5:
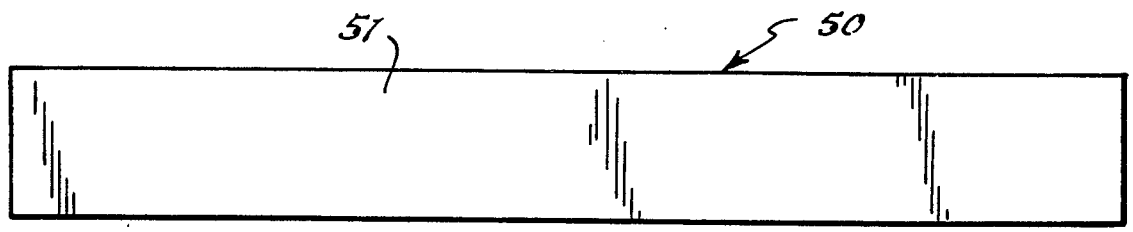
FIG. 5 is a plan view of the first step in the method of fabricating the securing tape of FIGS. 1-4.
Figure 6:
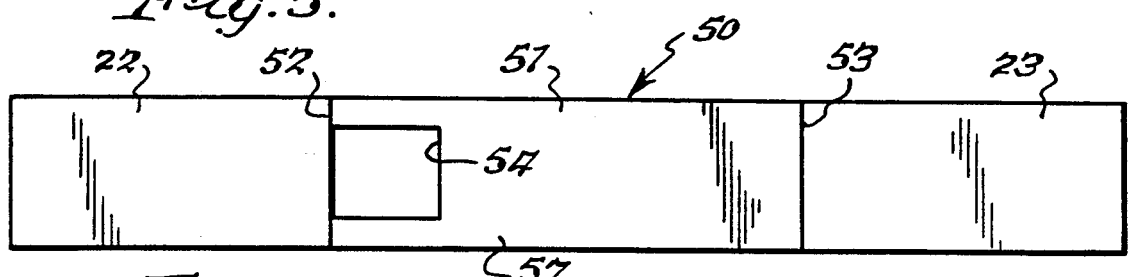
FIG. 6 is a plan view of the second and third steps in the manufacture of the securing tape.
Figure 7:
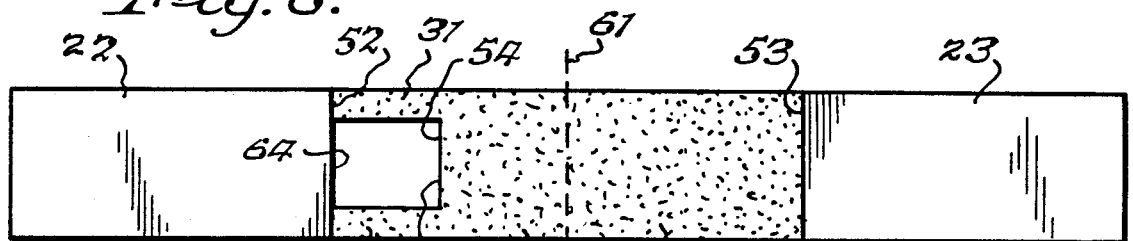
FIG. 7 is a plan view of the third step in the manufacture of the securing tape.

The securing tape 10 of the present invention includes a base portion 11 consisting of spaced parts 12 and 13 and an integral tab 16. Base portions 12 and 13 have outer surfaces 14 and 15, respectively, and inner surfaces 17 and 19, respectively, which have pressure-sensitive adhesive 20 and 21, respectively, thereon. The adhesive surfaces 20 and 21 are each completely covered by a strip of release paper 22 and 23, respectively, which are peeled off separately to expose the adhesive surfaces 20 and 21 when the base portion 11 is to be adhered to a surface 24 which may be a patient's skin.

The integral tab 16 extends away from portions 12 and 13 of base portion 11. In this respect, the side 27 of tab 16 is an integral extension of base portion 13 and the side 29 is an integral extension of base portion 14. Sides 27 and 29 are caused to adhere to each other by the adhesive on their inner surfaces, and they are integral continuations of each other by virtue of a return bend at edge 41. More specifically, there are two spaced strips 30 and 31 on tab side 29 which are integral extensions of side 14, and there is a cutout 32 between strips 30 and 31 which exposes the adhesive surface 33 on the surface on the inside of tab side 27. A sheet of release paper 34 adheres to adhesive surface 33 and covers it to prevent it from premature attachment to foreign objects, as is the case with release paper strips 22 and 23.

Hook and pile fabric portions 35 and 37, respectively, which are known under the trademark VELCRO are secured to tab 16 and base portion 12, respectively. In this respect, the hook portion 35 is secured in the position shown in FIG. 1 by its backing 39 of pressure-sensitive adhesive. The edge 40 (FIG. 1) of hook portion 35 falls short of the extreme edge 41 of tab 16 so as to leave a space 42 which can be grasped digitally to lift the tab from its operating position of FIG. 2 wherein the hook fabric 35 is in engagement with the pile fabric 37. The opposite edge 43 of hook fabric 35 terminates along the edge of exposed adhesive portion 33. The edge 44 of pile fabric 37 is located substantially at the opposite edge of exposed adhesive 33. The opposite edge 45 of pile fabric 37 is positioned as shown.

In use, the release paper 22 and 23 is removed from base portions 12 and 13, respectively, so that the pressure-sensitive adhesive 20 and 21 can be pressed against member 24. Thereafter, the release paper 34 is removed from overlying relationship with adhesive window 33, and the tube 25 or other foreign body is pressed against adhesive surface 33 in window 32 to locate it. Thereafter, tab 16 is folded downwardly from an upstanding position such as shown in FIG. 1 to a securing position such as shown in FIG. 2 to thereby firmly clamp tube 25 in position wherein the adhesive in window 32 positively immobilizes tube 25 against longitudinal or rotational movement. This is of extreme importance not only with a tube which enters a body cavity, but is also of extreme importance if the device 10 is used with an intravenous needle. If for any reason it is desired to reposition tube 25 or possibly place another tube onto securing tape 10, it is merely necessary to open tab 16 by separating the hook and pile fastener portions, remove the original tube 25 and replace it with another tube which is then both held in position by the hook and pile fastener and immobilized by the adhesive in the window. It is to be noted that the relationship between the hook and pile fabric, as shown, permits the securing tape 10 to accommodate tubes 25 of different sizes.

Figure 8:
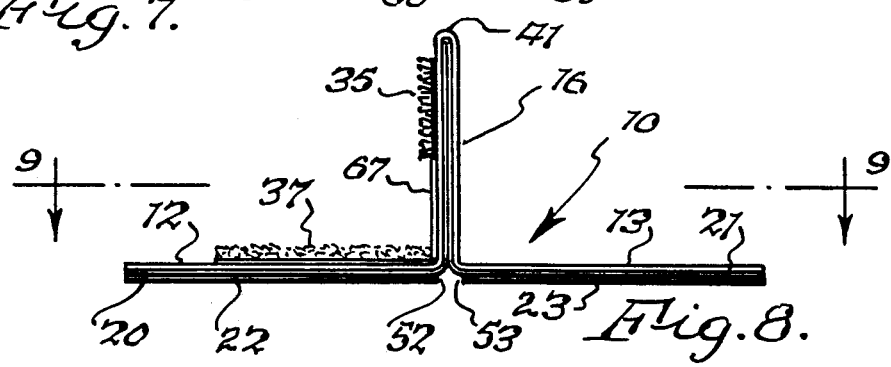
FIG. 8 is a side elevational view showing the fourth and fifth steps in the manufacture of the securing tape.
Figure 9:
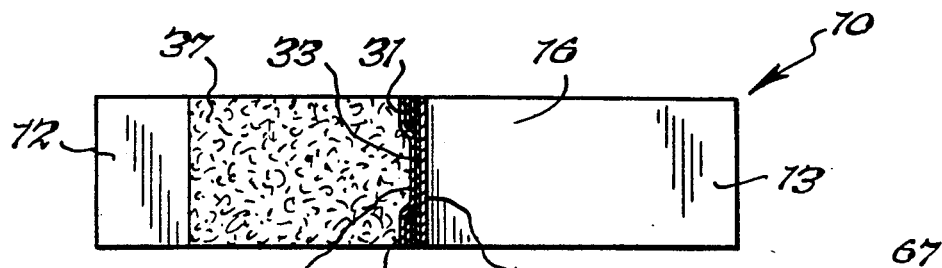
FIG. 9 is a cross sectional view taken substantially along line 9—9 of FIG.
Figure 10:
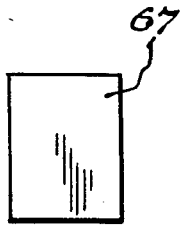
FIG. 10 is a plan view of the protective release paper which is secured to the exposed surface of the adhesive on the tab of the securing tape.

The method of fabricating the securing tape 10 described in FIGS. 1-4 is shown in FIGS. 5-10. The starting portion is a strip 50 of pressure-sensitive tape approximately eight inches long and one inch wide which has a release paper 51 covering its adhesive surface. The first step is to score the release paper 51 along lines 52 and 53. The next step is to cut out a block of the tape 50 adjacent scored line 52 to provide a window 54. The next step is to remove the release paper 57 between score lines 52 and 53 to expose the adhesive surface 59. Thereafter, the central portion 60 between score lines 52 and 53 is folded about its midpoint line 61 so that the portions of the adhesive surface on opposite sides of fold line 61 stick to each other and thus form tab 16, as shown in FIG. 8. At this time the release paper 22 and 23 adjacent score lines 52 and 53 will still be in covering relationship with the adhesive 20 and 21 on the portions of strip 50 which are now base portions 12 and 13. It can readily be seen that the strips 30 and 31 border cutout 54 and that the edges of cutout 54 are at 64 and 65. The next step is to secure hook portion 35 and pile portion 37 in the positions shown by pressure-sensitive adhesive thereon. The final step in the fabrication is to adhesively secure a release paper patch 67 across the portion of the adhesive surface 59 which is exposed through window or cutout 54.

The securing tape 10 has been depicted in the attitude of FIG. 1 as a matter of convenience for describing it. However, when it is packed for shipment, the parts can either be positioned with the hook and pile fastener portions in engagement with tab 16 lying across base portion 12, or, if desired, tab 16 can be positioned lying against tab portion 13. The tape 50 itself without release paper 51 thereon is approximately 0.007 of an inch thick and the release paper is approximately 0.006 of an inch thick. The material from which the securing tape 10 was fabricated is known under the trademark DUROPORE of the 3M Corporation and it has the grade designation 1538L. It is a porous pressure-sensitive hypoallergenic tape. It will be appreciated, of course, that other tapes can also be used.

While the preferred embodiment disclosed in the present application has shown the base portion 11 as having two portions 12 and 13 on opposite sides of tab 16, it will be appreciated that the concept of the present invention may also be practiced with a base having only a portion such as 12 facing the exposed adhesive 33 of the tab 16, and in such a configuration, the base portion 13 would be eliminated. The modification of this type is within the scope of the following claims.

While the preferred embodiment has disclosed the use of hook and pile fabric for fastening tab 16 to the base, another method of effecting such fastening is to provide another window of exposed adhesive outwardly on tab 16 from window 32 and this can be used to adhere tab 16 to the nonadhesive surface 14 of base member 12. Furthermore, if desired the additional exposed window of adhesive need not be a separate window but may be an extension of existing window 32.

In FIGS. 11-27 and 29 modifications of the above described medical securing tape are disclosed in the form of bandages for securing surgical or medical dressings as well as the previously described tubes or catheters.

The medical securing tape or bandage 70 of FIGS. 11 and 12 is shown as being adhesively secured to the skin 71 of a patient. In this respect, tape 70 is formed from a continuous strip of tape having a coating of adhesive on one side. Tape 70 includes a base portion 72 consisting of parts 73 and 74 and an integral tab 75. Base portions 73 and 74 have nonadhesive outer surfaces 77 and 79, respectively, and inner surfaces 80 and 81, respectively, which comprise pressure sensitive adhesive. Prior to the application of the securing tape 70 to the patient's skin 71, removable release paper (not shown) covers pressure sensitive adhesive surfaces 80 and 81, as described above relative to the embodiment of FIG. 1.

The integral tab 75 is formed in the same manner described above relative to integral tab 16 of FIG. 1. In this respect, the side 82 of tab 75 is an integral extension of base portion 73 and the side 83 is an integral extension of base portion 74. Sides 82 and 83 are caused to adhere to each other by the full coating of adhesive on their inner surfaces, which adhesive is a continuation of the adhesive surfaces 80 and 81. Sides 82 and 83 are connected to each other by the return bend 84 at the outer end of tab 75.

There is a cutout 85 in tab side 83 between portions 87 and 89 of continuous tape 90. There is a window or opening 91 in base portion 74 which is intended to receive a wound 92 when the securing tape or bandage 70 is applied to the patient's skin. A dressing 93, fragmentarily shown in FIG. 11, of the type normally used to cover wounds is intended to be placed in window 91 over wound 92. A resilient elastomeric foam-like pad is located in window 85 of tab 75 and is adhesively secured therein by pressure-sensitive adhesive 95 on the inside surface of tab side 82.

Hook and pile fasteners are utilized to secure tab 75 to base portion 74 in the same general manner as disclosed above in FIGS. 2 and 3. In this respect, hook fabric strips 97, 99 and 100 are adhesively secured to side 83 of tab 75, and pile strips 101, 102 and 103 are adhesively secured to side 79 of base portion 74. In the closed position hook fabric 97 meshes with pile fabric 101, hook portion 99 meshes with pile fabric 102, and hook fabric 100 meshes with pile fabric 103. Hook fabric strip 99 is spaced from return bend 84 to provide an end portion 98 which can be grasped when hook fabric strip 99 is to be separated from pile fabric strip 102 during the process of lifting tab 75 away from engagement with base portion 74. All of the following embodiments also have the feature of an end portion which can be grasped because the hook fabric is spaced from the extreme outer end of the tab.

The advantage of the securing tape or bandage 70 of FIGS. 11 and 12 is that the base portions can be adhesively secured to the patient's skin 71 and it can remain in position for a number of days. However, the dressings 93 can be replaced as frequently as desired without removing the bandage from the patient's skin 71 by merely lifting tab 75 to remove a dressing and returning tab 75 to a closed position after a new dressing 93 has been placed on wound 92.

Pad 94 is of solid rectangular configuration. Its purpose is to apply pressure to the dressing 93. However, if desired, other shapes of pads can be used instead of rectangular solid pad 94. For example, a pad 104 of FIG. 13 can be used which has a concave face 105 which faces the dressing with its opposite planar face adhesively secured to adhesive 95. Also if desired a pad, such as 107 of FIG. 15, can be used having a convex face 109 facing the dressing with its opposite planar face being adhesively secured to adhesive 95.

The bandage of FIG. 11 is formed to the shape shown in FIG. 11 from the blank 90 of FIG. 12 in the same manner described above in FIGS. 5-8 except that in FIG. 12 it is the nonadhesive outer surfaces of the adhesive strip which are shown whereas in FIG. 7 it is the adhesive side which faces the viewer.

Figure 15:
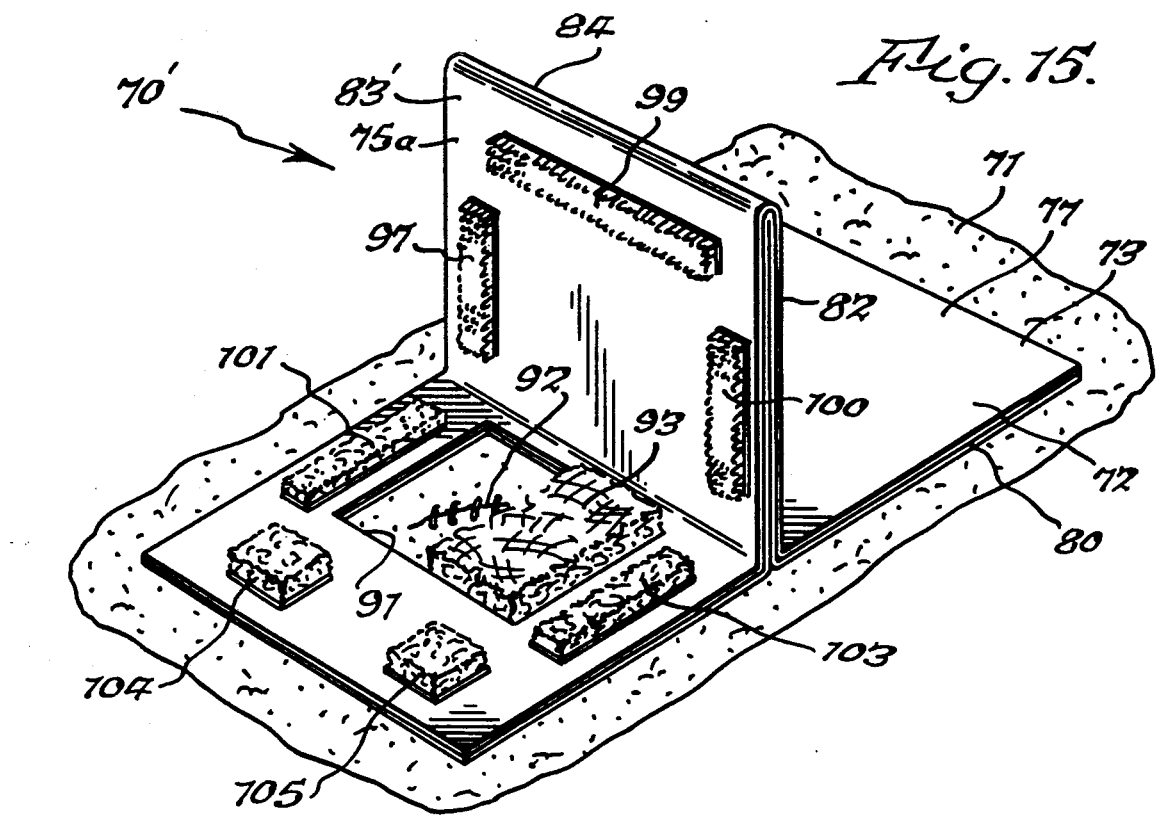
FIG. 15 is a fragmentary perspective view of another embodiment of a bandage for holding replaceable dressings against a wound.

In FIG. 15 a modified bandage 70' is disclosed wherein the only major difference over the bandage of FIG. 11 is that tab side 83' of tab 75a does not possess a window such as 85 to adhesively receive a pad, but a pad can be secured to the face of tab side 83' if desired by other means. A minor difference also is that pile fabric strip 102 of FIG. 11 is not used, and instead two pads 104 and 105 are used. Otherwise numerals in FIG. 15, which are the same as those of FIG. 11, represent identical elements of structure. The bandage 70' therefore can be used in situations where a pad such as 94 of FIG. 11 may not be required. However, bandage 70' is formed in the same basic manner as bandage 70, except for the window in tab 75a.

In FIGS. 16-19 a still further embodiment of the present invention is disclosed. The securing tape or bandage 110 is identical in all respects to that described in FIG. 11 except for (1) the placement of the hook and pile fabric fastening means and (2) the construction of base portion 74'. Accordingly, numerals which are identical to those used in FIG. 11 will represent like elements of structure in FIGS. 16-19. The base portion 74' of FIG. 16 differs from base 74 of FIG. 11 in that it contains a perforation 111 which permits the entire end portion 112 of base portion 74' to be torn all the way through along the perforation between the outermost edge of the base portion 112 and the window or opening 91, as depicted at 111' in FIG. 17.

The bandage 110 can be conveniently used with a drain or infusate tube 113 associated with wound 92. In this respect, in use the tube 113 overlies base portion 112 and is located between pile fabric portions 114 and 115 which meet with hook fabric portions 117 and 119, respectively, when tab 75' is in the closed position shown in FIG. 18. The spaced hook and pile portions delineate a channel 116 in which tube 113 lies, thereby not only causing the bandage to have a low profile when the tab is in a closed position but also limiting lateral movement of tube 113. A dressing (not shown) such as 93 of FIG. 11 overlies the wound 92 in window 91, and pad 94 provides pressure to the dressing.

The tab 75' also contains hook fabric portions 120 and 121 which mate with pile fabric portions 122 and 123 when tab 75 is in the closed position, and the tab 75' includes hook fabric portions 124 and 125 which mate with pile fabric portions 127 and 129 when the tab 75 is in the closed position. While not shown, a dressing is usually placed underneath drain tube 113 and overlying the end portion 112 of base 74' between pile fabric portions 114 and 115 to provide a cushion for tube 113.

The purpose of perforation 111 is to permit the end portion 112 of base 74' to be completely separated along the perforation 111 as partially shown in FIG. 17 to permit the bandage 110 to be removed from the skin without removing tube 113 from wound 92 in the event that tube 113 is connected to a drain bag or a bag of infusate. In this respect, end portion 112 is preferably separated along perforation 111 before base 72 is applied to the skin, and in use either portion of end portion 112 can be lifted away from the skin to completely separate this portion from its adjacent portion along the perforation to permit removal of bandage 110 without removing tube 113 from the wound or separating it from a bag. In addition, as can be seen from FIG. 17, tube 113 can be moved to a position 113a between pile fabric portions 122 and 123 or to a position 113b between pile fabric portions 127 and 129. This repositioning is sometimes necessary to avoid having the tube 113 overlie a particular area of the body for undesirably long periods of time. While the perforation 111 has been shown between pile fabrics 114 and 115, it will be appreciated that it can also or alternately be made between pile portions 122 and 123 and/or pile portions 127 and 129 so as to permit separation of the base portion 74' along such perforations. While a tube 113 has been shown, it will be appreciated that this embodiment will work in the same manner with other bodies such as a surgical needle which has been inserted into the skin.

The blank 130 (FIG. 19) from which the bandage 110 is formed is shown in FIG. 19, and it includes an opening or window 85 in side 83 of the tab and an opening or window 91 in base portion 74'. The view in FIG. 19 is the same as the view in FIG. 12 and the only difference between the two views is in the existence of perforation 111 in FIG. 19.

Figure 21:
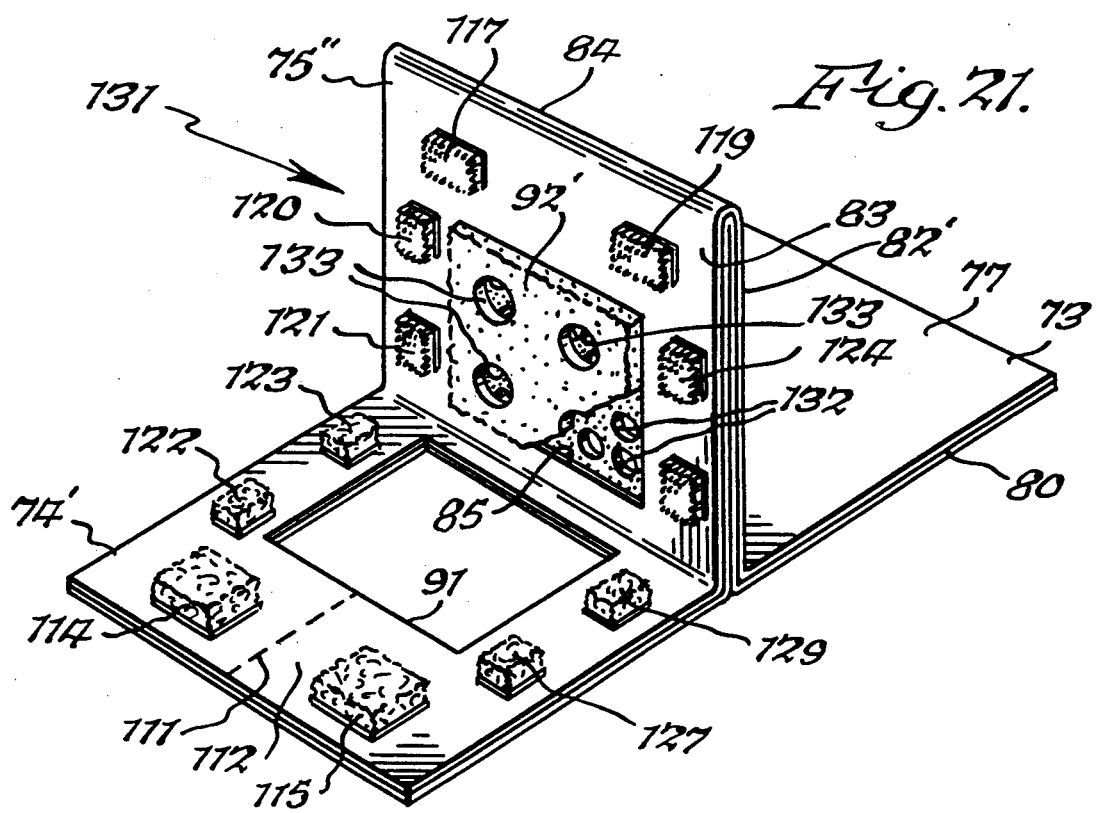
FIG. 21 is a perspective view of the bandage formed from the blank of FIG. 20.

In FIGS. 20 and 21 a still further embodiment of the present invention is disclosed. This embodiment is identical in all respects to the embodiment of FIGS. 16 and 17 except for the fact that the rear side 82' of the tab, which corresponds to the tab rear 82 of FIG. 17, is perforated with a plurality of openings in the form of perforations 132, and pad 92' has a plurality of openings therein in the form of perforations or apertures 133. Thus, when a dressing is placed into window 91 and tab 75" is closed, the dressing which overlies the wound within the window 91 will be exposed to the atmosphere through apertures 133 and perforations 132. Aside from the perforations 132 and apertured pad 92', the remaining parts of bandage 131 are identical to those described above relative to FIGS. 16-19, and like numerals are utilized to designate like parts. While the tab is shown as having circular perforations 132, it will be appreciated that the openings can be made in any desired shape, and this is the case with apertures 133 in the pad 92'. Also, the perforations 132 can be incorporated into the tab 75' of FIG. 15 so that a dressing held down by tab 75' without a pad, such as 94, can be exposed to the atmosphere.

Figure 22:
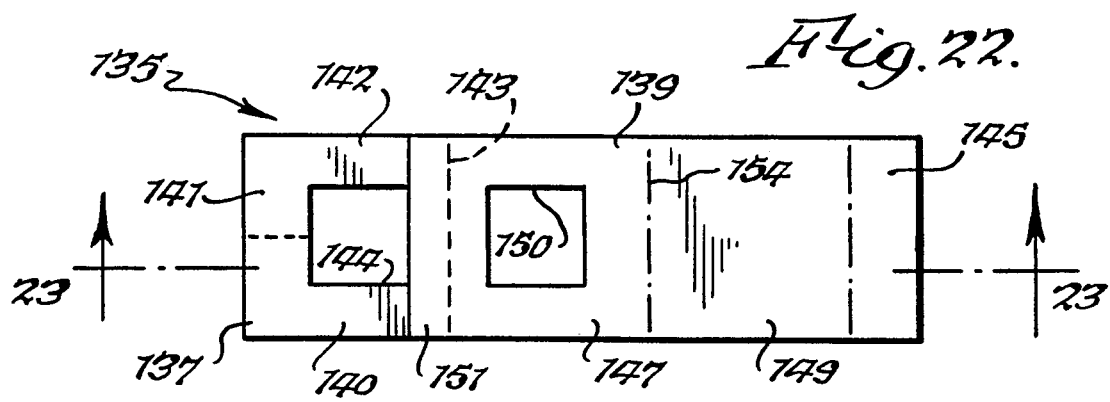
FIG. 22 is a plan view of two partially superimposed blanks of a two-piece bandage.
Figure 23:
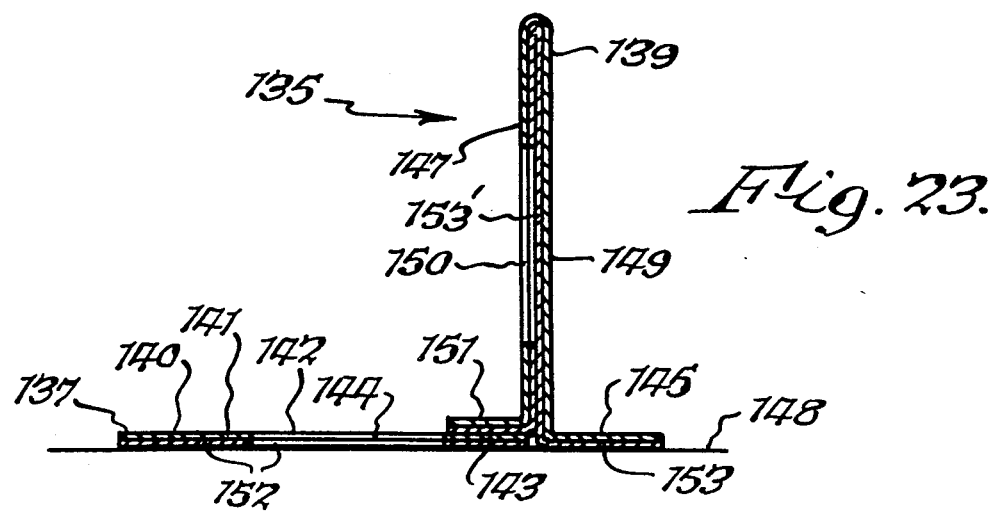
FIG. 23 is a cross sectional view taken substantially along line 23—23 of FIG. 22 and showing the assembled two-piece bandage with the tab in an elevated position.

In FIGS. 22 and 23 a still further modified bandage 135 of the present invention is disclosed. In this embodiment the bandage or securing tape is fabricated in two pieces, namely, a base 137 and a separate combined tab and base 139. More specifically, the base 137 includes sides 140, 141, 142 and 143 which surround opening or window 144 which is analogous to the above described window 91 which receives a dressing. The combined tab and base 139 includes a base portion 145 and a tab portion consisting of sides 147 and 149 with the former having a window 150. An additional base portion 151 is at the lower end of tab side 147. A pressure sensitive adhesive coating 152 is located on the complete underside of base portion 137, and an adhesive coating 153 is located on the underside of combined tab and base portion 139 so that when the tab sides 147 and 149 are folded about line 154 to the condition shown in FIG. 23, the adhesive portion 153' which is at window 50 will be used to adhesively receive and hold a pad such as 94 of FIG. 16. The hook and pile fastening means are not shown in FIG. 23 in the interest of brevity but it will be understood that these are applied to the securing tape, as described above, to maintain the side 147 of the flap in a closed position against base 140. As shown in FIG. 23, base portion 151 overlies base side 143 and is adhesively secured thereto by adhesive on the underside of base portion 151, and base portion 145 adheres to the skin 148 of the patient by the adhesive on its underside.

In FIGS. 24-27 a further bandage embodiment 157 is disclosed which is fabricated of two pieces, namely, a base portion 159 and a combined base and tab portion 160 (FIG. 25). The base portion 159 includes sides 161, 162, 163 and 164 which define a window 165. A pressure sensitive adhesive coating 167 is located on the underside of the base to secure it to the surface 169 of the patient's skin. The combined tab and base 160 includes an entire surface coated with pressure sensitive adhesive 170. The blank of FIG. 25 includes edge portions 171, 172 and 173. These edge portions 171, 172 and 173 are folded over to the condition shown in FIG. 26 to provide a window 174 through which the adhesive 170 is exposed and to which a pad 175 is adhered. The rear side 177 of the tab merges into a base portion 179 consisting of a portion 180 which is to be adhesively secured to the nonadhesive side 164 of base portion 159 and another portion 181 which extends beyond base portion 164 and is adhesively secured to the skin 169 of the patient. The hook and pile fasteners have been omitted, but they can be the same as in any of the other embodiments. As with the other embodiments, a dressing 182 is intended to be placed in window 165 to cover a wound. Also the base 159 may have a perforation 111 or a plurality of such perforations, as described above relative to FIGS. 16-19.

Figure 28:
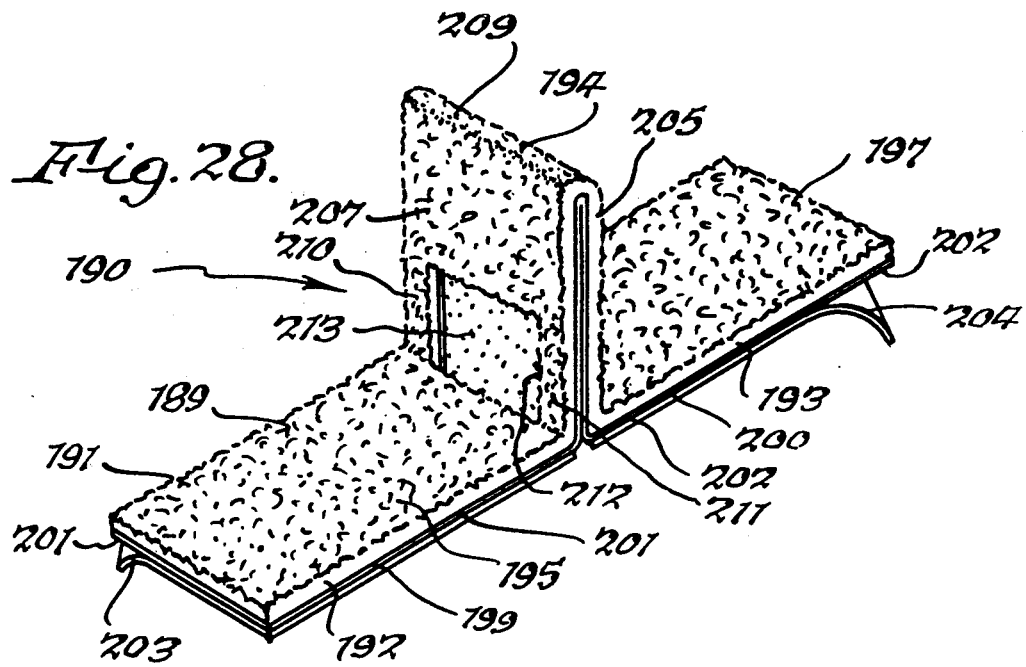
FIG. 28 is a perspective view of an alternate embodiment of the securing tape of FIGS. 1-10.

In FIG. 28 a modification 190 of the medical securing tape of FIGS. 1-10 is disclosed. Tape 190 differs from the tape 10 of FIGS. 1-10 in that it does not use separate hook fabric members and separate pile fabric members on the tab and base, respectively. Instead it uses a self-adhering fabric 189 which is essentially a combination of hook and pile fabric on each of the tab and base, and such fabric 189 will adhere to itself when separate pieces are pressed together, and such pieces can be pulled apart and reattached to each other repeatedly in the same manner as separate hook and pile fabric fasteners. The outer surface of the self-adhering fabric 189 can be of any suitable construction which will provide the self-adhering characteristic.

The securing tape 190 of FIG. 28, which consists of the above-described self-adhering fabric 189, includes a base portion 191 consisting of spaced sides 192 and 193 and an integral tab 194. Base portions 192 and 193 have outer surfaces 195 and 197, respectively, and inner surfaces 199 and 200, respectively, which have pressure-sensitive adhesive 201 and 202, respectively, thereon. The adhesive surfaces 201 and 202 are each completely covered by a strip of release paper 203 and 204, respectively, which are peeled off separately to expose the adhesive surfaces 201 and 202 when the base portion 191 is to be adhered to a patient's skin (not shown).

The integral tab 194 extends away from portions 192 and 193 of base portion 191. In this respect, the side 205 of tab 194 is an integral extension of base portion 193 and the side 207 is an integral extension of base portion 192. Sides 205 and 207 are caused to adhere to each other by the adhesive on their inner surfaces, and they are integral continuations of each other by virtue of a return bend at edge 209. More specifically, there are two spaced strips 210 and 211 on tab side 207 which are integral extensions of side 192, and there is a cutout 212 between strips 210 and 211 which exposes the adhesive surface 213 on the surface on the inside of tab side 205. A sheet of release paper (not shown), such as 34 of FIG. 1, adheres to adhesive surface 213 and covers it to prevent it from premature attachment to foreign objects, as is the case with release paper strips 203 and 204.

In use, the release paper 203 and 204 is removed from base portions 192 and 193, respectively, so that the pressure-sensitive adhesive 201 and 202 can be pressed against a person's skin. Thereafter, the release paper (not shown) is removed from overlying relationship with adhesive window 212, and a tube such as 25 of FIG. 2 or other foreign body is pressed against adhesive surface 213 in window 212 to locate it. Thereafter, tab 194 is folded downwardly from an upstanding position such as shown in FIG. 1 to a securing position such as shown in FIG. 2 to thereby firmly clamp tube 25 in position, as described in detail relative to the embodiment of FIGS. 1-10.

The embodiment of FIG. 28 is fabricated in substantially the same manner as described above and shown in FIGS. 5-8 relative to the embodiment of FIG. 1. The only difference is that there is no need to attach separate hook fabric and separate pile fabric to the parts which are to be attached to each other because the entire self-adhering fabric 189 is essentially a combination of hook and pile fabric, as described above.

Figure 29:
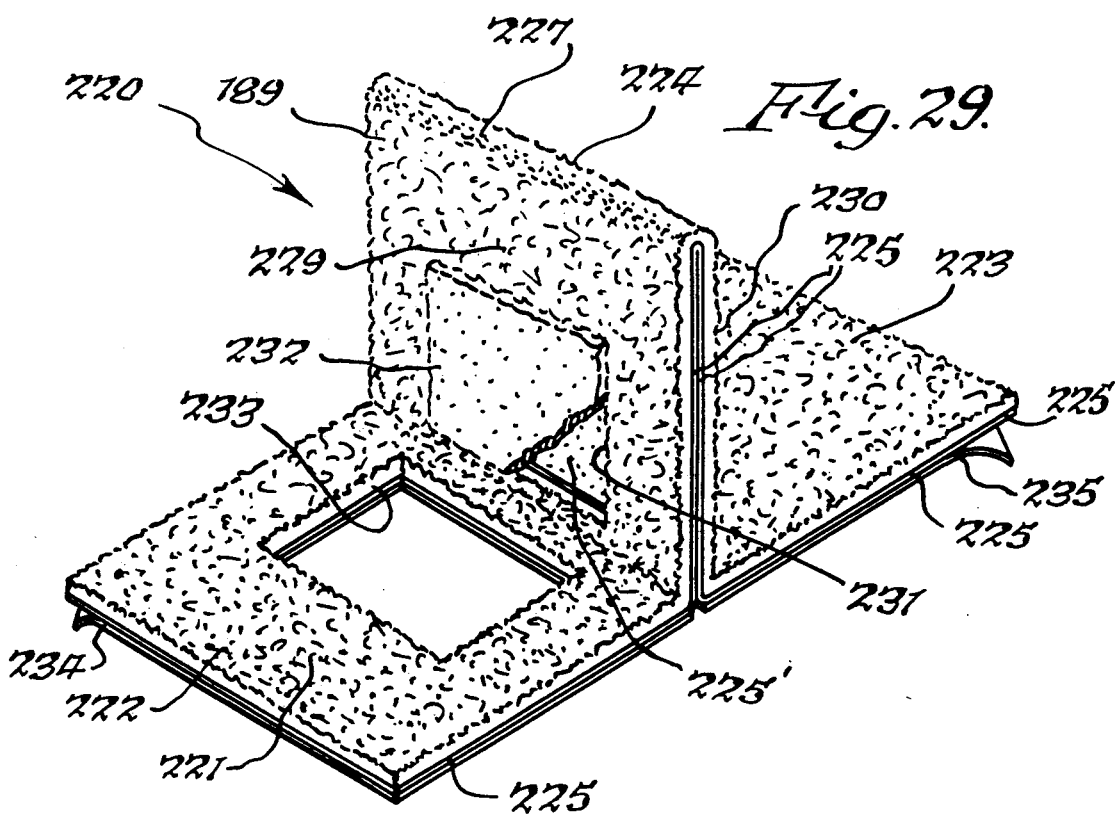
FIG. 29 is a perspective view of an alternate embodiment of the bandages of FIGS. 11-14, 16, 17 and 21.

In FIG. 29 an alternate embodiment 220 of the bandages of FIGS. 11-21 is disclosed. This embodiment, just like the embodiment of FIG. 28, is fabricated from a self-adhering tape 189 which is essentially a combination of hook and pile fabric material which will stick to itself. The specific bandage 220 is for holding a replaceable dressing, and it is fabricated in the same manner as described above relative to FIG. 11 except that it does not have the separate hook fabric fasteners and separate pile fabric fasteners.

The bandage 220 includes a base 221 consisting of spaced portions 222 and 223. A tab 224 is an integral extension of base portions 222 and 223. Tab 224 has a side 229 which is an integral extension of base portion 222, and it has a side 230 which is an integral extension of base portion 223. The fabric 189 has a continuous adhesive surface 225 which is located on the underside of base portions 222 and 223. Fabric 189 is doubled over at 227 to form tab 224 when adhesive on sides 229 and 230 adhere to each other as described above relative to FIGS. 1 and 28. There is a cutout 231 in tab side 229 to expose the adhesive portion 225' within cutout or window 231. A pad 232 which is of suitable resilient material, such as foam rubber or foam plastic, is adhesively secured to the adhesive within window or cutout 231. A cutout or window 233 is located in base portion 222 for receiving a replaceable dressing as described above relative to FIG. 11. When a dressing is located over a wound in window 233, tab 224 can be folded down so that pad 232 presses on the dressing, and tab 224 will be retained in a closed position because of the fact that the self-adhering fabric of the tab side 229 will adhere to the self-adhering fabric on base portion 222. Release paper 234 is located on the adhesive 225 on base side 222 and release paper 235 is located on the adhesive 225 on base side 223. The release paper is removed prior to causing base 221 to adhere to the skin of a person.

Figure 16:
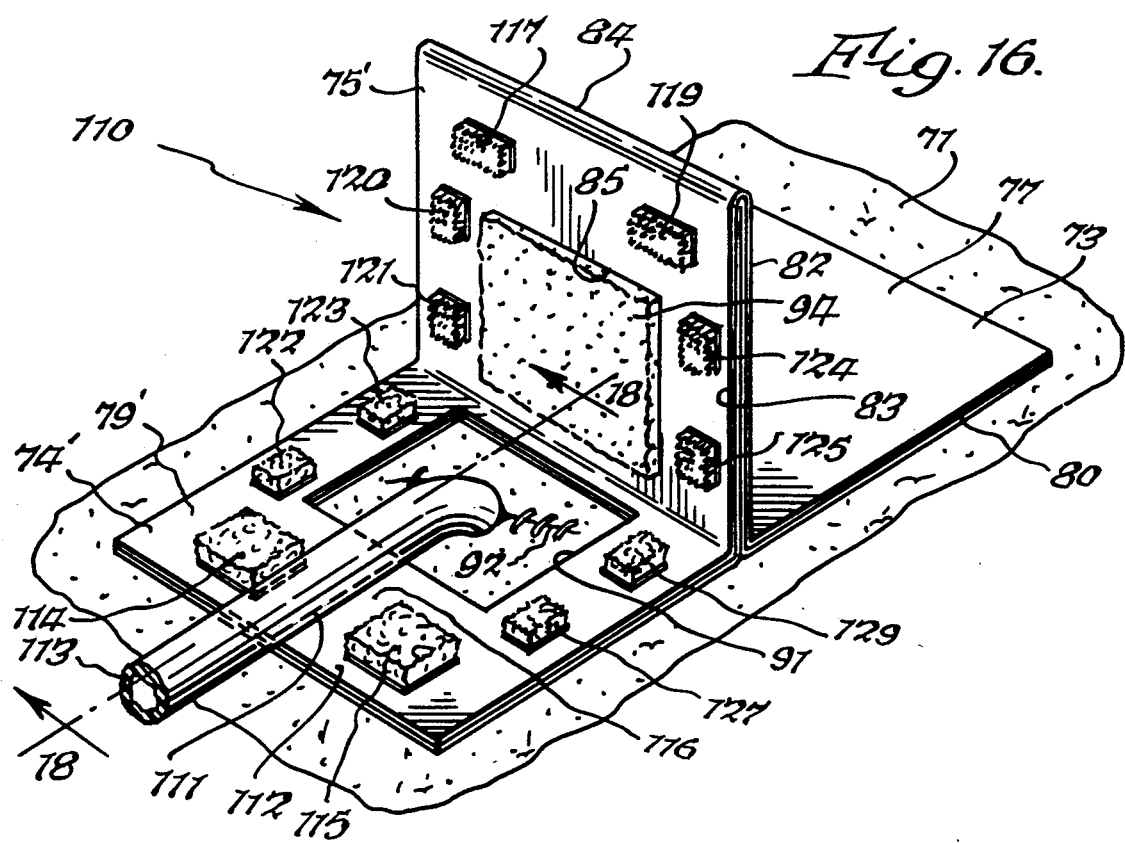
FIG. 16 is a fragmentary perspective view of still another embodiment of a bandage used in conjunction with a fluid tube installed in a patient.

While not specifically shown in FIG. 29, an embodiment utilizing the combination self-adhering fabric 189 of FIG. 29 can incorporate the feature of FIGS. 16 and 17, namely, a perforation such as 111 which permits the base portion 222 to be separated to pass around a tube such as 113. Also, the structure of FIG. 29 permits a tube 113 to be moved to different positions such as shown in FIG. 17. Additionally, if desired the embodiment of FIG. 29 can include perforations in the tab, such as perforations 132 of FIG. 20, and it can incorporate an apertured pad such as 92' having apertures 133, as shown in FIG. 21, to expose a dressing to the air. Also the embodiment of FIG. 15 with no opening exposing adhesive to receive a pad can be fabricated from the self-adhering fabric 189. In fact the embodiment of FIG. 29 using self-adhering tape can incorporate any of the features of the previous embodiments which are not inconsistent with its basic structure.

While the outer surfaces of the tapes of FIGS. 28 and 29 have been described above as self-adhering fabric in which the securing means is essentially a combination of hook and pile fabric, it will be appreciated that the outer surfaces can be of any suitable construction which permits repeated attaching and separating and may include by way of example and not of limitation any type of fuzzy material or a coating of cohesive glue which will cause the tab and base to removably stick to each other but not to foreign bodies. It will be appreciated that the securing tapes and bandages having alternate types of outer surfaces can include the features of the various embodiments of the present invention which are not inconsistent therewith.

While all of the above described features of all embodiments of the invention are not shown in association with each individual embodiment, it will be appreciated that each of the features can be used with each of the embodiments unless it is inconsistent therewith. For example, as noted above, the perforations 132 in the tab, as shown in FIGS. 20 and 21, can be incorporated into all of the embodiments including that of FIG. 15, and the embodiments which incorporate a pad on the tab can have the tab apertured, as shown in FIG. 21, to cooperate with the perforations in the tab. Furthermore, all embodiments which use hook and pile fabric fasteners may have the hook fasteners and pile fasteners in spaced positions, as shown in FIG. 16 to receive a tube therebetween.

Summarizing, all embodiments of the improved securing tape or bandage of the present invention have the advantage of the tab comprising a folded-over portion of an adhesive tape. In certain embodiments a portion of the folded-over portion of the tab is exposed to provide an adhesive window for receiving a pad. Certain embodiments also have the advantage of permitting the bandage to be removed without removing an overlying tube which may be connected to a drain bag or an infusate bag. In addition, certain embodiments are made with two pieces rather than a single piece whereby either the base portion or the tab portion may be removed and replaced by another like portion.

While preferred embodiments of the present invention have been disclosed, it will be appreciated that it is not limited thereto but may be otherwise embodied with the scope of the following claims.

What is claimed is:

1. A method of fabricating a bandage for securing to a patient's skin comprising the steps of providing a strip of pressure-sensitive tape having a pressure-sensitive adhesive surface and a nonadhesive surface with release paper overlying the pressure-sensitive adhesive surface, cutting first and second spaced openings in said pressure-sensitive tape, removing the release paper from a central portion of said pressure-sensitive tape surrounding said first opening, folding the central portion of said pressure-sensitive tape from which said release paper was removed back on itself to provide a tab with a portion of said pressure-sensitive surface being exposed through said first opening, securing a pad to said pressure-sensitive surface exposed through said first opening, the remainder of said pressure-sensitive tape other than said tab providing a base having said second opening for surrounding a wound and for receiving a dressing, and applying securing means to said pressure-sensitive tape for securing said tab to said nonadhesive surface of said base with said first and second openings overlying each other.

2. A method as set forth in claim 1 including the step of cutting first perforation means in said central portion in spaced relationship to said first spaced opening so that said perforation means is aligned with said first opening when said central portion of said tape is folded back on itself, and providing second perforation means in said pad in alignment with said first perforation means.

3. A method as set forth in claim 1 including the step of providing means for selectively separating a portion of said base between an outer edge thereof and said second opening.

4. A method of fabricating a bandage for securing to a patient's skin comprising the steps of providing a strip of pressure-sensitive tape having a pressure-sensitive adhesive surface and a nonadhesive surface and an end portion and an adjacent portion of said tape adjacent to said end portion, cutting an opening in said end portion of said pressure-sensitive tape, and folding said adjacent portion of said pressure-sensitive tape back on itself to provide a tab, the remainder of said pressure-sensitive tape other than said tab but including said end portion providing a base with said opening in said end portion for surrounding a wound and for receiving a dressing.

5. A method as set forth in claim 4 including the step of providing perforation means in said tab for alignment with said opening in said base when said tab is secured to said base for permitting said opening to be exposed to the atmosphere through said perforation means in said tab when said tab overlies said end portion of said tape.

6. A method as set forth in claim 5 including the step of providing means for selectively separating a portion of said base between an outer edge thereof and said second opening.

7. A method as set forth in claim 4 including the step of providing means for selectively separating a portion of said base between an outer edge thereof and said second opening.

8. A method as set forth in claim 4 including the step of cutting a second opening in said adjacent portion of said tape so that when said adjacent portion of said tape is folded back on itself the adhesive surface on a portion of said adjacent portion is exposed through said second opening, and securing a pad to said adhesive which is exposed through said second opening.

9. A method as set forth in claim 8 including providing means for selectively separating a portion of said end portion between an outer edge thereof and said opening.

10. A method as set forth in claim 8 including the step of applying securing means to said pressure-sensitive tape for securing said tab to said end portion.

11. A method as set forth in claim 8 including the step of providing perforation means in said tab for alignment with said opening in said base when said tab is secured to said base for permitting said opening to be exposed to the atmosphere through said perforation means in said tab when said tab overlies said end portion of said tape.

12. A method as set forth in claim 11 including providing means for selectively separating a portion of said end portion between an outer edge thereof and said opening.

13. A method as set forth in claim 12 including the step of applying securing means to said pressure-sensitive tape for securing said tab to said end portion.

14. A method as set forth in claim 13 wherein said nonadhesive surface comprises self-adhering fabric.

15. A method as set forth in claim 14 including the step of cutting a second opening in said adjacent portion of said tape so that when said adjacent portion of said tape is folded back on itself the adhesive surface on a portion of said adjacent portion is exposed through said second opening, and securing a pad to said adhesive which is exposed through said second opening.

16. A method as set forth in claim 4 wherein said nonadhesive surface comprises self-adhering fabric.

17. A method as set forth in claim 4 including the step of applying securing means to said pressure-sensitive tape for securing said tab to said end portion.

* * * * *